(12) United States Patent
Ryu et al.

(10) Patent No.: US 9,143,250 B2
(45) Date of Patent: Sep. 22, 2015

(54) BLOOD GLUCOSE MONITORING SYSTEM HAVING WIRELESS COMMUNICATION MODULE TO WHICH TIME SYNCHRONIZATION METHOD IS APPLIED

(71) Applicant: i-SENS, Inc., Seoul (KR)

(72) Inventors: Chang Woo Ryu, Gyeonggi-do (KR); Dae Kag Choi, Gyeonggi-do (KR); Geun Sig Cha, Seoul (KR); Hakhyun Nam, Seoul (KR)

(73) Assignee: I-SENS, INC., Seoul (KR)

( * ) Notice: Subject to any disclaimer, the term of this patent is extended or adjusted under 35 U.S.C. 154(b) by 0 days.

(21) Appl. No.: 14/273,405

(22) Filed: May 8, 2014

(65) Prior Publication Data

US 2014/0241338 A1    Aug. 28, 2014

Related U.S. Application Data

(63) Continuation of application No. PCT/KR2012/008746, filed on Oct. 24, 2012.

(30) Foreign Application Priority Data

Nov. 11, 2011    (KR) .......................... 10-2011-0117620

(51) Int. Cl.
*A61B 5/15* (2006.01)
*H04J 3/06* (2006.01)
(Continued)

(52) U.S. Cl.
CPC ............... *H04J 3/0638* (2013.01); *A61B 5/002* (2013.01); *A61B 5/14532* (2013.01);
(Continued)

(58) Field of Classification Search
CPC ... H04L 43/50; H04L 12/2697; H04L 7/0016; H04J 3/0638; G06Q 50/22; G06Q 50/24; A61B 5/002; A61B 5/14532; A61B 5/150854; A61B 5/157; A61B 5/1411; A61B 5/15022; G04G 21/025; G04G 7/00; G04G 21/04; G04G 9/0076; G06F 19/00; H04W 56/00
USPC ......... 370/320, 343, 350, 503, 235, 389, 392, 370/395.4, 321, 508–510; 455/522.1, 455/556.1; 340/539.12, 573.1; 709/238, 709/242, 248; 714/48, 55, 746, 748, 814, 714/815; 600/316, 319, 347, 365
See application file for complete search history.

(56) References Cited

U.S. PATENT DOCUMENTS 6,760,309 B1 * 7/2004 Rochberger et al. .......... 370/235
7,448,996 B2 * 11/2008 Khanuja et al. ............... 600/300
(Continued)

FOREIGN PATENT DOCUMENTS

| JP | 2004-008457 | * | 1/2004 | ............... A61B 5/00 |
| JP | 2009-183692 | | 8/2009 | |
| KR | 10-2008-0074786 | | 8/2008 | |

OTHER PUBLICATIONS

TS 101 626 V6.0.0, Digital cellular telecommunications system(Phase 2+); Network Identity and Timezone (NITZ); Service description, Stage 1 (GSM 02.42 version 6.0.0 Release 1997), Apr. 1999, 9 Pages.*

(Continued)

*Primary Examiner* — Edan Orgad
*Assistant Examiner* — Ivan O Latorre
(74) *Attorney, Agent, or Firm* — Klarquist Sparkman, LLP

(57) ABSTRACT

The present disclosure relates to a blood sugar meter system with a wireless communication module, and more particularly, to a time synchronization method between a blood sugar meter system with a wireless communication module synchronized with a cellular network such as a global system for mobile communication (GSM)/code division multiple access (CDMA) network and the cellular network. The present invention provides a blood sugar meter system with a wireless communication module applying a time synchronization scheme including: a global system for mobile communication (GSM)/code division multiple access (CDMA) network transmitting network identity and time zone (NITZ) information; and a blood sugar meter metering user's blood sugar data, wherein the blood sugar meter synchronizes a network time according to the NITZ information with an internal time of the metered data and transmits the metered blood sugar data to a server connected to the GSM/CDMA network.

9 Claims, 3 Drawing Sheets

(51) Int. Cl.

| | |
|---|---|
| *G06Q 50/24* | (2012.01) |
| *A61B 5/00* | (2006.01) |
| *A61B 5/145* | (2006.01) |
| *G04G 21/02* | (2010.01) |
| *G04G 21/04* | (2013.01) |
| *G04G 7/00* | (2006.01) |
| *G04G 9/00* | (2006.01) |
| *A61B 5/157* | (2006.01) |

(52) U.S. Cl.
CPC ........... *A61B 5/150854* (2013.01); *G04G 7/00* (2013.01); *G04G 9/0076* (2013.01); *G04G 21/025* (2013.01); *G04G 21/04* (2013.01); *G06Q 50/24* (2013.01); *A61B 5/1411* (2013.01); *A61B 5/157* (2013.01); *A61B 5/150022* (2013.01)

(56) References Cited

U.S. PATENT DOCUMENTS

| | | | |
|---|---|---|---|
| 2004/0179523 A1* | 9/2004 | Maruyama et al. | 370/389 |
| 2005/0038680 A1* | 2/2005 | McMahon | 705/3 |
| 2006/0002236 A1* | 1/2006 | Punkka | 368/21 |
| 2007/0093786 A1* | 4/2007 | Goldsmith et al. | 604/890.1 |
| 2007/0217291 A1* | 9/2007 | Jeong et al. | 368/21 |
| 2008/0032736 A1 | 2/2008 | Bari et al. | |
| 2008/0194934 A1 | 8/2008 | Ray et al. | |
| 2009/0058635 A1* | 3/2009 | LaLonde et al. | 340/539.11 |
| 2009/0103735 A1* | 4/2009 | Aizu et al. | 380/278 |
| 2009/0163793 A1* | 6/2009 | Koehler et al. | 600/365 |
| 2011/0205064 A1* | 8/2011 | Strachan et al. | 340/573.1 |
| 2011/0224505 A1* | 9/2011 | Sadhu | 600/301 |
| 2012/0151093 A1* | 6/2012 | Zheng | 709/248 |
| 2012/0192254 A1* | 7/2012 | Garcia Perez et al. | 726/4 |
| 2012/0207029 A1* | 8/2012 | Kanda et al. | 370/242 |
| 2014/0227794 A1* | 8/2014 | Choi et al. | 436/95 |

OTHER PUBLICATIONS

International Search Report from International Patent Application No. PCT/KR2012/008746, dated Mar. 25, 2013, 5 pages.

\* cited by examiner

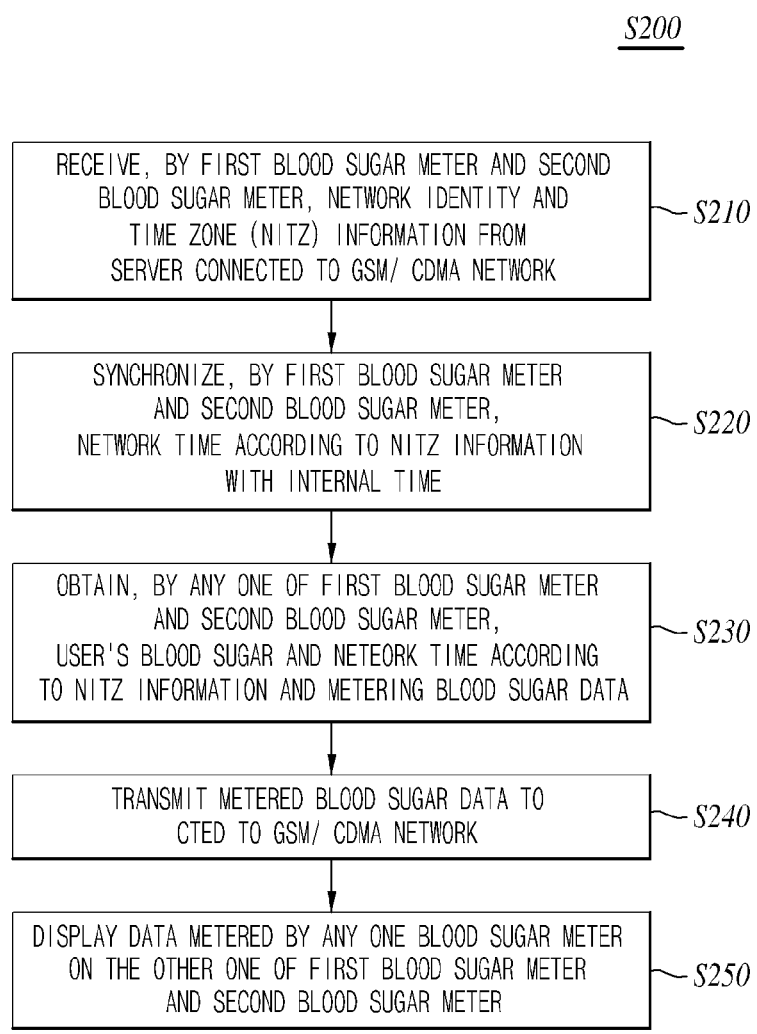

BLOOD GLUCOSE MONITORING SYSTEM HAVING WIRELESS COMMUNICATION MODULE TO WHICH TIME SYNCHRONIZATION METHOD IS APPLIED

CROSS REFERENCE TO RELATED APPLICATIONS

This application is a continuation of International Patent Application No. PCT/KR2012/008746, filed Oct. 24, 2012, which claims the benefit of Korean Patent Application No. 10-2011-0117620, filed Nov. 11, 2011, both of which are incorporated herein by reference in their entirety.

TECHNICAL FIELD

The present disclosure relates to a blood sugar meter system with a wireless communication module, and more particularly, to a time synchronization method between a blood sugar meter system with a wireless communication module synchronized with a cellular network such as a global system for mobile communication (GSM)/code division multiple access (CDMA) network and the cellular network.

BACKGROUND ART

In general, a wireless communication terminal in a blood sugar meter system based on an asynchronous transmission mode receives local time zone information (i.e., standard time of a specific region) from a local base station of a public land mobile network (PLMN) and receives changed local standard time information from a corresponding local base station if the wireless communication terminal moves to another time zone. Thus, a wireless communication terminal user has to adjust the reference time of the wireless communication terminal in person.

In order to resolve inconvenience that the wireless communication terminal user in the mobile communication system based on the asynchronous transmission mode has to adjust the reference time of a mobile communication terminal in person as described above, there is a method of receiving network identity and time zone (NITZ) information from the PLMN to update the reference time of the wireless communication terminal.

The wireless communication terminal in the wireless communication system based on the asynchronous transmission mode receives the NITZ information from the PLMN in the following cases: 1) when the wireless communication terminal registers with the PLMN, 2) when the wireless communication terminal moves to another local time zone, 3) when the local time zone of the PLMN is changed, 4) when the network identity of the PLMN is changed, and 5) when the wireless communication terminal sets up a call with (accesses) the PLMN.

According to the method of updating the reference time of the wireless communication terminal in the wireless communication system based on a typical asynchronous transmission mode, when the NITZ information is received form the PLMN as described above, a message "NITZ information has been received. Do you want to change the system time of the wireless communication terminal according to new NITZ information" is displayed on the screen of the display unit of the wireless communication terminal, and then when a user of the wireless communication terminal inputs a command to change the system time of the wireless communication terminal (selects a 'yes' key), the wireless communication terminal reboots and automatically updates the system time of the wireless communication terminal based on the new NITZ information.

However, the method of updating the reference time in the wireless communication module based on the typical asynchronous transmission mode as described above has a limitation in that it involves inconvenience of use because a device including the wireless communication module has to be rebooted in order to automatically update the reference time of the wireless communication module according to the new NITZ information.

Also, a blood sugar meter with the wireless communication module focuses on the function of transmitting blood sugar metering data and ignores the actual effective components of the metered blood sugar metering data.

In particular, when there is a certain difference between when blood sugar is metered and when a metering value is transmitted, and when several times in the same country such as North America have certain differences, a metered time varies depending on where a user is, and when information on a time difference between where a server collecting blood sugar metering data is and where a blood sugar meter is used is not checked, management becomes complex.

Disclosure of the Invention Technical Problem

One object of the present invention is to provide a time synchronization method between a cellular network and a blood sugar meter system with a wireless communication module that synchronizes the time of the blood sugar meter system with the cellular network such as GSM/CDMA to enable a server receiving a blood sugar metering value to compare a time when a user actually meters blood sugar with when the metered value is transmitted and may accordingly determine the effectiveness of the blood sugar metering value.

Technical Solution

In order to achieve the objects, the present invention provides a blood sugar meter system with a wireless communication module applying a time synchronization scheme including: a global system for mobile communication (GSM)/code division multiple access (CDMA) network transmitting network identity and time zone (NITZ) information; and a blood sugar meter metering user's blood sugar data, wherein the blood sugar meter synchronizes a network time according to the NITZ information with an internal time of the metered data and transmits the metered blood sugar data to a server connected to the GSM/CDMA network.

The present invention also provides a blood sugar meter system with a wireless communication module applying a time synchronization scheme including: a global system for mobile communication (GSM)/code division multiple access (CDMA) network transmitting network identity and time zone (NITZ) information; a first blood sugar meter metering blood sugar data of a user residing in a first time zone, wherein the first blood sugar meter synchronizes a network time according to the NITZ information with an internal time of the metered data and transmits the metered blood sugar data to a server connected to the GSM/CDMA network; and a first blood sugar meter metering blood sugar data of a user residing in a second time zone, wherein the first blood sugar meter synchronizes a network time according to the NITZ information with an internal time of the metered data and transmits the metered blood sugar data to a server connected to the GSM/CDMA network, wherein the first blood sugar meter and the second blood sugar meter are time-zone synchronized with a time according to the NITZ information transmitted from the GSM/CDMA network.

Furthermore, the present invention provides a data transmission method of a blood sugar meter system with wireless communication module applying a time synchronization scheme including receiving, by a blood sugar meter, network identity and time zone (NITZ) information from a server connected to global system for mobile communication (GSM)/code division multiple access (CDMA) network; synchronizing a network time according to the NITZ information with an internal time of the metered data; obtaining user's blood sugar and metering blood sugar data; and transmitting the metered blood sugar data to a server connected to the GSM/CDMA network.

Furthermore, the present invention also provides a data transmission method of a blood sugar meter system with a wireless communication module applying a time synchronization scheme including receiving, by a first blood sugar meter and a second blood sugar meter, network identity and time zone (NITZ) information from a server connected to a global system for mobile communication (GSM)/code division multiple access (CDMA) network; synchronizing, by the first blood sugar meter and the second blood sugar meter, an internal time with a network time according to the NITZ information to correspond to the network time; obtaining, by any one of the first blood meter and the second blood sugar meter, user's blood sugar and metering blood sugar data; transmitting metered blood sugar data to a server to the GSM/CDMA network; and displaying data metered by the any one blood sugar meter on the other one of the first blood sugar meter and the second blood sugar meter.

Advantageous Effects

According to the present invention, since a user does not manipulates the time set-up of a blood sugar meter in person, it is possible to increase user convenience when using the blood sugar meter and it is possible to determine data effectiveness through the difference between when blood sugar is actually metered and a time from a wireless communication module.

Also, since a user in a region where there are several time zones and daylight saving is performed such as North America does not need to set a time depending on his/her residing region or season, there is an effect in that it is possible to enhance the accuracy of blood sugar metering data depending on a residing region and season.

BRIEF DESCRIPTION OF THE DRAWINGS

FIG. 4 is a flow chart of a data transmission method applied to the system shown in FIG. 2.

MODE FOR CARRYING OUT THE INVENTION

Figure 1:
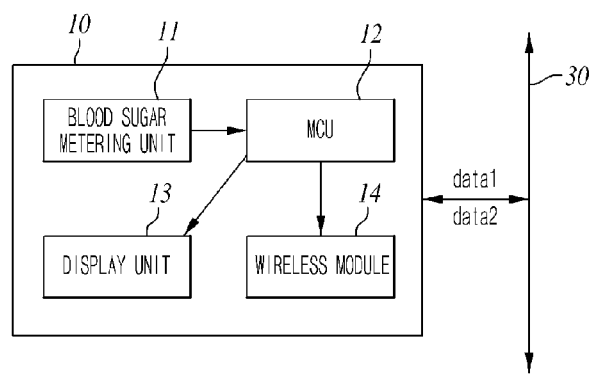
FIG. 1 is a block diagram of a blood sugar meter system with a wireless communication module applying a time synchronization scheme according to an embodiment of the present invention.

A blood sugar meter system with a wireless communication module applying a time synchronization scheme according to an embodiment of the present invention includes a global system for mobile communication (GSM)/code division multiple access (CDMA) network transmitting network identity and time zone (NITZ) information; and a first blood sugar meter metering blood sugar data of a user residing in a first time zone, wherein the first blood sugar meter synchronizes a network time according to the NITZ information with an internal time of the metered data and transmits the metered blood sugar data to a server connected to the GSM/CDMA network.

A blood sugar meter system with a wireless communication module applying a time synchronization scheme according to another embodiment of the present invention includes a global system for mobile communication (GSM)/code division multiple access (CDMA) network transmitting network identity and time zone (NITZ) information; a first blood sugar meter metering blood sugar data of a user residing in a first time zone, wherein the first blood sugar meter synchronizes a network time according to the NITZ information with an internal time of the metered data and transmits the metered blood sugar data to a server connected to the GSM/CDMA network; and a first blood sugar meter metering blood sugar data of a user residing in a second time zone, wherein the first blood sugar meter synchronizes a network time according to the NITZ information with an internal time of the metered data and transmits the metered blood sugar data to a server connected to the GSM/CDMA network, wherein the first blood sugar meter and the second blood sugar meter are time-zone synchronized with a time according to the NITZ information transmitted from the GSM/CDMA network.

The blood sugar meter includes a micro control unit (MCU) metering user's blood sugar information; a display unit displaying the blood sugar data metered by the MCU; and a wireless communication module synchronizing a time according to the NITZ information transmitted from the GSM/CDMA network with a metering time according to the blood sugar data metered by the MCU to transmit to the GSM/CDMA network.

The wireless communication module is of a CDMA or GSM scheme.

The first and the second blood sugar meters are synchronized with a time of the server connected to the GSM/CDMA network.

The first and the second blood sugar meters are synchronized with a time according to data transmitted while they are located.

A data transmission method of a blood sugar meter system with wireless communication module applying a time synchronization scheme according to an embodiment of the present invention includes receiving, by a blood sugar meter, network identity and time zone (NITZ) information from a server connected to global system for mobile communication (GSM)/code division multiple access (CDMA) network; synchronizing a network time according to the NITZ information with an internal time of the metered data; obtaining user's blood sugar and metering blood sugar data; and transmitting the metered blood sugar data to a server connected to the GSM/CDMA network.

The receiving includes setting up a call with a local base station for a region where a user currently stays; and receiving corresponding local standard time information from the call set-up local base station.

The local standard time information is information varying when a time varies according to daylight saving or season.

The synchronizing includes storing received local standard time information; and setting up a reference time according to stored local standard time information.

A data transmission method of a blood sugar meter system with a wireless communication module applying a time synchronization scheme according to another embodiment of the present invention includes receiving, by a first blood sugar meter and a second blood sugar meter, network identity and time zone (NITZ) information from a server connected to a global system for mobile communication (GSM)/code division multiple access (CDMA) network; synchronizing, by the first blood sugar meter and the second blood sugar meter, an internal time with a network time according to the NITZ information to correspond to the network time; obtaining, by any one of the first blood meter and the second blood sugar meter, user's blood sugar and metering blood sugar data; transmitting metered blood sugar data to a server to the GSM/CDMA network; and displaying data metered by the any one blood sugar meter on the other one of the first blood sugar meter and the second blood sugar meter.

The receiving includes setting up a call with a local base station for a region where a user currently stays; and receiving corresponding local standard time information from the call set-up local base station.

The synchronizing includes storing received local standard time information; and setting up a reference time according to stored local standard time information.

The local standard time information is information varying when a time varies according to daylight saving or season.

The particular structural or functional descriptions of embodiments according to the concepts of the present invention disclosed in the specification or the application are only intended for the purpose of describing embodiments according to the concepts of the present invention and the embodiments according to the concepts of the present invention may be practiced in various forms and should not be construed as being limited to those described in the specification or the application.

Since the present invention may make various modifications and have several embodiments, particular embodiments will be illustrated in the drawings and described in the detailed description in detail. However, it is not intended to limit the present invention to particular embodiments but it should be understood that the present invention covers all modifications, equivalents, and/or replacements that fall within the spirit and technical scope of the present invention.

Although the terms a first and a second may be used to describe various components, these components should not be limited by these terms. The terms may be named only for the purpose of distinguishing one component from another component, e.g., a first component may be named as a second component without departing from the scope of right according to the concepts of the present invention and similarly, a second component may also be named as a first component.

When any component is referred to as being 'connected' to another component, it should be understood that the former can be 'directly connected' to the latter, or there may be another component in between. On the contrary, when any component is referred to as being 'directly connected' to another component, it should be understood that there may be no other component in between. Other expressions describing the relationship between components, such as "between" and "directly between" or "adjacent to" and "adjacent directly to" should be also construed in the same way.

The terms used herein are only used to describe specific embodiments and not intended to limit the present invention. In the following embodiments, the terms in singular form may include the plural form unless otherwise specified. It should be understood that the terms "includes" or "has" indicate the presence of characteristics, numbers, steps, operations, components, parts or combinations thereof represented in the present disclosure but do not exclude the presence or addition of one or more other characteristics, numbers, steps, operations, components, parts or combinations thereof.

Unless otherwise defined herein, all terms used herein including technical or scientific terms have the same meanings as those generally understood by a person skilled in the art. Terms defined in dictionaries generally used should be construed to have meanings matching with contextual meanings in the related art and are not construed as an ideal or excessively formal meaning unless otherwise defined herein.

Exemplary embodiments of the present invention are described below in detail with reference to the accompanying drawings.

FIG. 1 represents a blood sugar meter system with a wireless communication module applying a time synchronization scheme according to an embodiment of the present invention.

As shown in FIG. 1, a system 100 of the present invention includes a global system for mobile communication (GSM)/code division multiple access (CDMA) network server 30 and a blood sugar meter 10.

The GSM/CDMA network server 30 transmits network identity and time zone (NITZ) information to the blood sugar meter.

The blood sugar meter 10 meters user's blood sugar data, and synchronizes a network time according to the NITZ information with an internal time of the metered data and transmits the metered blood sugar data to the GSM/CDMA network server 30.

More particularly, the blood sugar meter 10 includes a blood sugar metering unit 11, a micro control unit (MCU) 12, a display unit 13, and a wireless communication module 14.

The blood sugar metering unit 11 meters information on user's blood sugar and may include a bio-sensor.

The MCU 12 converts a blood sugar value metered from the blood sugar meter 11 and transmits the value obtained through the conversion to the wireless communication module 14.

The display unit 13 displays the metered blood sugar data converted into digital codes by the MCU 12.

The wireless communication unit 14 synchronizes a time according to the NITZ information transmitted from the GSM/CDMA network server 30 with a metering time according to the blood sugar data converted into the digital codes by the MCU 12, and transmits to the GSM/CDMA network server.

Figure 2:
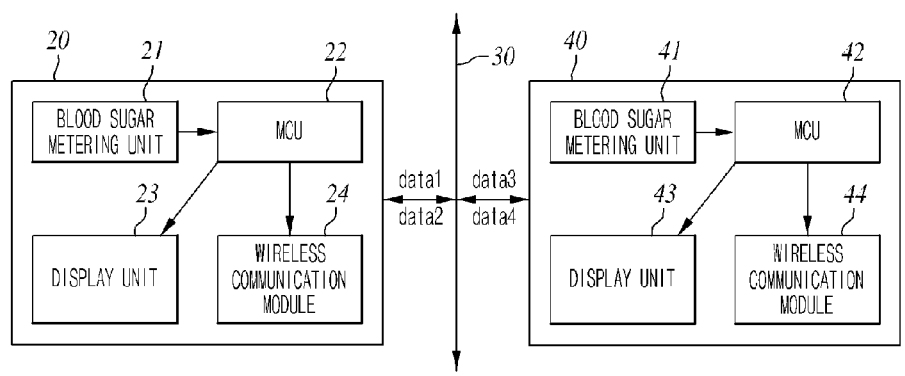
FIG. 2 is a block diagram of a blood sugar meter system with a wireless communication module applying a time synchronization scheme according to another embodiment of the present invention.

FIG. 2 is a block diagram of a blood sugar meter system with a wireless communication module applying a time synchronization scheme according to another embodiment of the present invention.

As shown in FIG. 2, the system 200 of the present invention includes the GSM/CDMA network server 30, a first blood sugar meter 20, and a second blood sugar meter 40.

The GSM/CDMA network server 30 transmits the NITZ information to each of the first blood sugar meter 20 and the second blood sugar meter 40.

The first blood sugar meter 20 meters blood sugar data of a user residing in a first time zone, synchronizes a network time according to the NITZ information with an internal time of the metered data and transmits the metered blood sugar data to a server connected to the GSM/CDMA network.

The second blood sugar meter 40 meters blood sugar data of a user residing in a second time zone, synchronizes a network time according to the NITZ information with an internal time of the metered data and transmits the metered blood sugar data to a server connected to the GSM/CDMA network.

The first blood sugar meter 20 and the second blood sugar meter 40 are time-zone synchronized with a time according to the NITZ information transmitted from the GSM/CDMA network.

More particularly, the first and the second blood sugar meters 20 and 40 include blood sugar metering units 21 and 41 metering user's blood sugar information, MCUs 22 and 42 converting blood sugar values metered from the blood sugar metering units into digital data, display units displaying the metered blood sugar data converted by the MCUs 22 and 42, and wireless communication modules 24 and 44 that synchronize a time according to the NITZ information transmitted from the GSM/CDMA network with a metering time according to the blood sugar data metered by the MCUs 22 and 42, and transmit the metered blood sugar data to the GSM/CDMA network.

The wireless communication modules may be of a CDMA or GSM scheme but is not limited thereto.

Also, the first blood sugar meter 20 and the second blood sugar meter 40 may be synchronized with a time of the GSM/CDMA network server 30, and synchronize the first time zone and the second time zone with a time zone according to the NITZ information by using the time according to the NITZ information transmitted from the GSM/CDMA network server as a reference time.

The first blood sugar meter 20 and the second blood sugar meter 40 may be synchronized with a time according to data transmitted while they are located.

Figure 3:
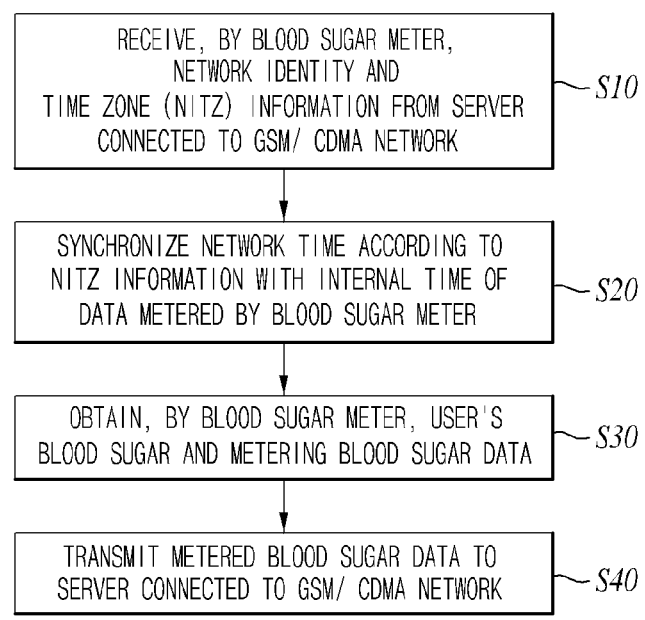
FIG. 3 is a flow chart of a data transmission method applied to the system shown in FIG. 1.

FIG. 3 is a flow chart of a data transmission method applied to the system shown in FIG. 1.

As shown in FIG. 3, the data transmission method of the present invention includes receiving, by the blood sugar meter, the NITZ information from a server connected to the GSM/CDMA network in step S10; synchronizing a network time according to the NITZ information with an internal time of the metered data in step S20; obtaining user's blood sugar and metering blood sugar data in step S30; and transmitting the metered blood sugar data to the server connected to the GSM/CDMA network in step S40.

The receiving in step S10 includes setting up a call with a local base station for a region where a user currently stays; and receiving corresponding local standard time information from the call set-up local base station.

In this example, the local standard time information may be information varying when a time varies according to daylight saving or season.

The synchronizing in step S20 may include storing the received local standard time information and setting up a reference time according to the stored local standard time information.

FIG. 4 is a flow chart of a data transmission method applied to the system shown in FIG. 2.

The data transmission method according to another embodiment of the present invention includes receiving, by the first blood sugar meter and the second blood sugar meter, NITZ information from the server connected to the GSM/CDMA network in step S210; synchronizing, by the first blood sugar meter and the second blood sugar meter, an internal time with a network time according to the NITZ information to correspond to the network time in step S220; obtaining, by any one of the first blood sugar meter and the second blood sugar meter, user's blood sugar and metering blood sugar data in step S230; transmitting the metered blood sugar data to the server connected to the GSM/CDMA network in step S240; and displaying the data metered by the any one blood sugar meter on the other one of the first blood sugar meter and the second blood sugar meter in step S250.

The receiving in step S210 includes setting up a call with a local base station for a region where a user currently stays; and receiving corresponding local standard time information from the call set-up local base station.

The synchronizing in step S220 may include storing the received local standard time information and setting up a reference time according to the stored local standard time information, in which the local standard time information may be information varying when a time varies according to daylight saving or season.

According to the present invention, since a user does not manipulates the time set-up of a blood sugar meter in person, it is possible to increase user convenience when using the blood sugar meter and it is possible to determine data effectiveness through the difference between when blood sugar is actually metered and a time from a wireless communication module.

Also, since a user in a region where there are several time zones and daylight saving is performed such as North America does not need to set a time depending on his/her residing region or season, there is an effect in that it is possible to enhance the accuracy of blood sugar metering data depending on a residing region and season.

Embodiments of the present disclosure disclosed in the specification and the drawings merely present specific examples to easily describe the technical details of the present disclosure and help to understand the present disclosure and are not intended to limit the scope of the present disclosure. It is obvious to a person skilled in the art to which the present invention pertains that other variations based on the technical spirit of the present invention in addition to the embodiments described above may be made.

INDUSTRIAL APPLICABILITY

According to the present invention, since a user does not manipulates the time set-up of a blood sugar meter in person, it is possible to increase user convenience when using the blood sugar meter and it is possible to determine data effectiveness through the difference between when blood sugar is actually metered and a time from a wireless communication module. Also, since a user in a region where there are several time zones and daylight saving is performed such as North America does not need to set a time depending on his/her residing region or season, there is an effect in that it is possible to enhance the accuracy of blood sugar metering data depending on a residing region and season. Thus, the present invention may be useful for the blood sugar meter.

We claim:

1. A blood sugar meter system with a wireless communication module applying a time synchronization scheme, the blood sugar meter system comprising:

a blood sugar meter that meters a user's blood sugar data, wherein the blood sugar meter synchronizes an internal time of the metered blood sugar data to a network time of a residence area of the user according to network identity and time zone (NITZ) information transmitted from a global system for mobile communication (GSM)/code division multiple access (CDMA) network, and when a local standard time changes depending on a season change, modifies the network time of the user's residence area according to the changed time; and a server connected to the GSM/CDMA network to receive the metered blood sugar data from the blood sugar meter, wherein the server determines whether the metered blood sugar data is valid or not, by comparing a time for the blood sugar meter to meter a datum of the blood sugar data with a time for transmitting said datum of the metered blood sugar data, and upon determining the blood sugar datum to be invalid, notifies the blood sugar meter of the same.

2. The blood sugar meter system as set forth in claim 1, wherein the blood sugar meter comprises:
 a blood sugar metering unit metering the user's blood sugar data;
 a micro control unit (MCU) converting the blood sugar data metered from the blood sugar metering unit into digital data;
 a display unit displaying the metered blood sugar data converted by the MCU; and
 a wireless communication module synchronizing an internal time of the blood sugar data metered by the blood sugar metering unit to a network time according to the NITZ information transmitted from the GSM/CDMA network and transmitting to a server connected to the GSM/CDMA network.

3. The blood sugar meter system as set forth in claim 1, wherein the local standard time change is associated with Daylight Saving Time.

4. The blood sugar metering system of claim 1, further comprising the global system for mobile communication (GSM) code division multiple access (CDMA) network that transmits the network identity and time zone (NITZ) information.

5. A blood sugar meter system with a wireless communication module applying a time synchronization scheme, the blood sugar meter system comprising:
 a first blood sugar meter that meters blood sugar data for a user residing in a first time zone, wherein the first blood sugar meter synchronizes an internal time of the metered data to a network time of a residence area of the user according to network identity and time zone (NITZ) information transmitted from a global system for mobile communication (GSM)/code division multiple access (CDMA) network;
 a second blood sugar meter that meters blood sugar data of a user residing in a second time zone, wherein the second blood sugar meter synchronizes an internal time of the metered data to a network time according to the NITZ information transmitted from the GSM/CDMA network; and
 a server connected to the GSM/CDMA network to receive the metered blood sugar data from the first and second blood sugar meters, respectively,
 wherein, when a local standard time changes depending on seasons, the first and second blood sugar meters modify the network time of the user's residence area according to the changed time, and
 the server determines whether the metered blood sugar data is valid or not, by comparing a time for the first and second blood sugar meters to meter respective first and second blood sugar data with a time for transmitting the respective first and second metered blood sugar data, and when determining the blood sugar data to be invalid, notifies the blood sugar meter of the same.

6. The blood sugar meter system as set forth in claim 5, wherein each of the blood sugar meters comprises:
 a blood sugar metering unit metering the user's blood sugar data;
 a micro control unit (MCU) converting the blood sugar data metered from the blood sugar metering unit into digital data;
 a display unit displaying the metered blood sugar data converted by the MCU; and
 a wireless communication module synchronizing an internal time of the blood sugar data metered by the blood sugar metering unit to a network time according to the NITZ information transmitted from the GSM/ CDMA network and transmitting to a server connected to the GSM/CDMA network.

7. The blood sugar meter system as set forth in claim 5, wherein the local standard time change is associated with Daylight Saving Time.

8. The blood sugar metering system of claim 5, further comprising the global system for mobile communication (GSM) code division multiple access (CDMA) network that transmits the network identity and time zone (NITZ) information.

9. A blood sugar metering system, comprising:
 a server connected to a global system for mobile communication (GSM)/code division multiple access (CDMA) network that transmits network identity and time zone (NITZ) information, the server coupled to the GSM/CDMA network to receive a metered blood sugar datum from a blood sugar meter, the metered blood sugar datum including a blood sugar value and a time associated with acquisition of the blood sugar value, wherein the server determines whether the metered blood sugar datum is valid or not by comparing the time associated with acquisition of the blood sugar datum with a time at which the blood sugar datum is transmitted by the blood sugar meter via the GSM/CDMA network, and if the blood sugar data is determined to be invalid, notifies the blood sugar meter of the same.

* * * * *